US012575936B2

(12) United States Patent
Zhu et al.

(10) Patent No.: US 12,575,936 B2
(45) Date of Patent: Mar. 17, 2026

(54) OXIDE LAYER-CONTAINING ZIRCONIUM-NIOBIUM ALLOY ANKLE JOINT PROSTHETIC SYSTEM AND MANUFACTURING METHOD

(71) Applicant: Just Medical Devices (Tianjin) Co., Ltd., Tianjin (CN)

(72) Inventors: Xiaojing Zhu, Tianjin (CN); Jieru Huang, Tianjin (CN); Ping Ye, Tianjin (CN); Jing Zhao, Tianjin (CN); Lu Liu, Tianjin (CN)

(73) Assignee: Just Medical Devices (Tianjin) Co., Ltd., Tianjin (CN)

( * ) Notice: Subject to any disclaimer, the term of this patent is extended or adjusted under 35 U.S.C. 154(b) by 386 days.

(21) Appl. No.: 17/916,711

(22) PCT Filed: Jun. 21, 2021

(86) PCT No.: PCT/CN2021/101284
§ 371 (c)(1),
(2) Date: Oct. 3, 2022

(87) PCT Pub. No.: WO2022/088702
PCT Pub. Date: May 5, 2022

(65) Prior Publication Data
US 2024/0138995 A1     May 2, 2024

(30) Foreign Application Priority Data

Oct. 30, 2020    (CN) ........................... 202011195113.3

(51) Int. Cl.
*A61F 2/42*        (2006.01)
*B22F 10/20*       (2021.01)
(Continued)

(52) U.S. Cl.
CPC ............ *A61F 2/4202* (2013.01); *B22F 10/20* (2021.01); *C22C 16/00* (2013.01); *C23C 8/12* (2013.01);
(Continued)

(58) Field of Classification Search
CPC ............ A61F 2/4202; A61F 2002/4205; B22F 10/20; B22F 2005/005; B22F 3/15;
(Continued)

(56) References Cited

U.S. PATENT DOCUMENTS

2016/0305005 A1    10/2016  Walker
2023/0248879 A1*    8/2023  Su ......................... A61F 2/4014
(Continued)

FOREIGN PATENT DOCUMENTS

CN        102048600 A       5/2011
CN        104087729 A      10/2014
(Continued)

OTHER PUBLICATIONS

International Search Report of PCT/CN2021/101284.
Written Opinion of PCT/CN2021/101284.

*Primary Examiner* — Bruce E Snow

(57) ABSTRACT

The present disclosure discloses an ankle prosthesis containing zirconium-niobium alloy on oxidation layer and a preparation method thereof, the preparation method comprises: using zirconium-niobium alloy powder as a raw material, conducting a 3D printing for one-piece molding to obtain an intermediate products of the talus part and tibial part, and performing Sinter-HIP, cryogenic cooling and surface oxidation to obtain talus part and tibial part. The talus part is connected with the tibial part in a sliding mode; a bone trabeculae is respectively arranged on the lower surface of the talus body and the outer surfaces of the two first fixations, and on the upper surface of the tibial body and
(Continued)

the outer surfaces of the two second fixations as well, so as to improve bone ingrowth.

6 Claims, 11 Drawing Sheets

(51) Int. Cl.
| | | |
|---|---|---|
| *C22C 16/00* | (2006.01) | |
| *C23C 8/12* | (2006.01) | |
| *B33Y 10/00* | (2015.01) | |
| *B33Y 70/00* | (2020.01) | |
| *B33Y 80/00* | (2015.01) | |

(52) U.S. Cl.
CPC ....... *A61F 2002/4205* (2013.01); *B33Y 10/00* (2014.12); *B33Y 70/00* (2014.12); *B33Y 80/00* (2014.12)

(58) Field of Classification Search
CPC .......... B22F 10/64; B22F 10/66; C22C 16/00; C22C 1/0458; C23C 8/12; C23C 8/10; B33Y 10/00; B33Y 70/00; B33Y 80/00; B33Y 40/20; C22F 1/002; C22F 1/186
See application file for complete search history.

(56) References Cited

U.S. PATENT DOCUMENTS

| | | | | |
|---|---|---|---|---|
| 2023/0338615 A1* | 10/2023 | Liu | ........................ | B33Y 40/20 |
| 2023/0380877 A1* | 11/2023 | Dean | ........................ | A61B 34/10 |
| 2024/0138995 A1* | 5/2024 | Zhu | ........................ | C22C 1/0458 |

FOREIGN PATENT DOCUMENTS

| | | |
|---|---|---|
| CN | 109330748 A | 2/2019 |
| CN | 109674561 A | 4/2019 |
| CN | 110742711 A | 2/2020 |
| CN | 111826603 A | 10/2020 |
| CN | 112274301 A | 1/2021 |

* cited by examiner

OXIDE LAYER-CONTAINING ZIRCONIUM-NIOBIUM ALLOY ANKLE JOINT PROSTHETIC SYSTEM AND MANUFACTURING METHOD

CROSS-REFERENCE TO RELATED APPLICATIONS

This application is a national stage application of PCT/CN2021/101284. This application claims priorities from PCT Application No. PCT/CN2021/101284, filed Jun. 21, 2021, and from the Chinese patent application 202011195113.3 filed Oct. 30, 2020, the content of which are incorporated herein in the entirety by reference.

TECHNICAL FIELD

The present disclosure relates to the technical field of artificial ankle joint, in particular to the ankle prosthesis containing zirconium-niobium alloy on oxidation layer and its preparation method.

BACKGROUND TECHNOLOGY

Arthroplasty is one of the effective procedures for the treatment of end-stage diseases. However, after the joint prosthesis has been implanted into the human body for a long time, soft materials, such as ultra-high molecular weight polyethylene (UHMWPE), will produce a large number of wear debris particles due to the wear of the articular surface under the long-term action of the complex physiological and mechanical environment in the body. The accumulation of wear debris can cause a series of tissue reactions, leading to osteolysis, aseptic loosening and prosthesis failure. Moreover, metal joint materials such as cobalt chromium alloy, nickel titanium alloy and stainless steel alloy will release toxic metal ions under the long-term joint action of internal friction and corrosion, such as Cr, Ni, Mn, Mo and V ions, which will cause allergic reaction and other unknown potential hazards.

Zirconium-niobium alloy has been gradually used in the field of medical devices for its excellent corrosion resistance, mechanical properties and good biocompatibility. Zirconium-niobium alloy can react with N, C, O or other elements to form a hard oxidation layer on the surface. It has excellent wear resistance and low wear rate, which can reduce the wear of soft materials, that is, it has excellent wear resistance of joint articular surface. Moreover, the oxidation layer can reduce the release of metal ions and has excellent biocompatibility, that is, excellent biocompatibility at the osseointegration interface. The low wear rate of the articular surface is combined organically with the osseointegration interface (trabecula), which has excellent bone ingrowth performance, enabling the prosthesis to achieve the advantages of both interfaces at the same time.

Currently, the artificial prostheses used in clinical practice include bone cement fixation prosthesis and cementless fixation prosthesis. Studies have shown that the high temperature generated by the cemented prosthesis during the solidification of bone cement will cause the death of some bone cells so as to affect the bone growth. Cementless fixation prosthesis has been widely used due to its good bone growth performance. The osseointegration interface of cementless prosthesis is usually sprayed with hydroxyapatite coating or titanium coating, which has the advantage of overcoming the high temperature during the solidification of bone cement conductive to the growth of bone cells, and the disadvantage is that the surface coating is easy to fall off, which affects the use effect and will cause surgical failure in extreme cases. With the development of 3D printing technology, porous metal bone trabeculae made of 3D printing technology provided on the surface of prosthesis in contact with host bone tissue can solve the problem of coating falling off, and also can realize bone ingrowth instead of bone growth. However, the solid part of the 3D printing products have the problems such as uneven microstructure and internal defects, resulting in poor mechanical properties. The failure of powder fusion in part of trabecular structure also results in poor mechanical properties.

Therefore, it is of great significance to fabricate an ankle prosthesis containing zirconium-niobium alloy on oxidation layer with excellent mechanical properties and realize the advantages of two interfaces.

SUMMARY OF THE DISCLOSURE

One of the objectives of the present disclosure is to overcome the deficiencies of the existing technology to provide an ankle prosthesis containing zirconium-niobium alloy on oxidation layer.

The second purpose of the present disclosure is to provide a preparation method of the ankle prosthesis containing zirconium-niobium alloy on oxidation layer.

The technical scheme of the present disclosure is summarized as follows:

The preparation method of ankle prosthesis containing zirconium-niobium alloy on oxidation layer includes the following steps:

1) Using zirconium-niobium alloy powder as the raw material, conducting a 3D printing for one-piece molding, and obtaining a first intermediate of talus part and a first intermediate of tibial part respectively, putting the two first intermediates into the Sinter-HIP furnace, heating to 1250° C.-1400° C. under helium/argon gas protection, placing at a constant pressure of 140 MPa-180 MPa for 1 h to 3 h, reducing to a normal pressure, cooling to below 200° C. with the furnace, taking them out, and obtaining a second intermediate of talus part and a second intermediate of tibial part;

2) Placing two second intermediate products in a programmable thermostat to cool to −80° C. to −120° C. at a rate of 1° C./min, keeping them at a constant temperature for 5 h to 10 h, and taking them out of the programmed thermostat; placing them in a liquid nitrogen for 16 h to 36 h, and adjusting the temperature to a room temperature so as to obtain a third intermediate of talus part and a third intermediate of tibial part;

3) Placing two third intermediate products in a programmable thermostat to cool to −80° C. to −120° C. at a rate of 1° C./min, and placing them at a constant temperature for 5 h to 10 h, taking them out of the programmed thermostat, placing them in the liquid nitrogen for 16 h to 36 h and adjusting the temperature to room temperature so as to obtain a fourth intermediate of talus part and a fourth intermediate of tibial part;

4) Machining, finishing, polishing, cleaning, and drying the fourth intermediate products, and obtaining a fifth intermediate of talus part and a fifth intermediate of tibial part; the roughness of the upper surface of the fifth intermediate product of the talus part and the lower surface of the fifth intermediate product of the tibial part is Ra≤0.050 μm;

5) Placing the two fifth intermediate products in a tube furnace, introducing normal-pressure helium/argon gas containing 5% to 15% of oxygen in percentage by mass, heating to 500° C. to 700° C. at 5° C./min to 20° C./min, and cooling down to 400° C. to 495° C. at 0.4° C./min to 0.9° C./min; and cooling to be below 200° C. sequentially, taking them out to obtain the talus part and tibial part.

The structure of the talus part is the same as its first intermediate, second intermediate, third intermediate, fourth intermediate and fifth intermediate.

The structure of the tibial part is the same as its first intermediate, second intermediate, third intermediate, fourth intermediate, and fifth intermediate.

The ankle prosthesis containing zirconium-niobium alloy on oxidation layer comprises a talus part 1 and a tibial part 2, the talus part 1 comprises a talus body 4 and two first fixations 3 arranged at the front and rear direction of the lower surface of the talus body 4.

The tibial part 2 comprises a tibial body 5 and two second fixations 6 arranged at the front and rear direction of the upper surface of the tibial body 5.

The talus part 1 is connected with the tibial part 2 in a sliding mode.

A bone trabeculae 7 is arranged on the lower surface of the talus body 4 and the outer surfaces of the two first fixations 3, and the bone trabeculae 7 is arranged on the upper surface of the tibial body 5 and the outer surfaces of the two second fixations 6 as well, the pore size of the bone trabeculae 7 ranges from 0.35 mm-1.10 mm, the porosity ranges from 55% to 78%, through-hole ratio is 100%, and the thickness ranges from 0.5 mm-3 mm.

The chemical composition of the zirconium-niobium alloy powder in percentage by mass is respectively 85.6%-96.5% of Zr, 1.0%-12.5% of Nb, and the rest are unavoidable impurities; where a particle size of the zirconium-niobium alloy powder ranges from 45 to 150 μm.

The specific steps for adjusting the temperature in steps 2) and 3) are: increasing the temperature to −120° C. to −80° C. and keeping the constant temperature for 3 h to 5 h; then increasing the temperature to −40° C. to −20° C. and keeping the constant temperature for 3 h to 5 h and then increasing the temperature to 4° C. to 8° C. and keeping the constant temperature for 1 h to 3 h and then increasing the temperature.

The ankle prosthesis containing zirconium-niobium alloy on oxidation layer prepared by the above method.

Compared with the existing technical solutions, the present disclosure has the following beneficial effects:

The bone trabeculae of the ankle prosthesis containing zirconium-niobium alloy on oxidation layer of the present disclosure are integrated with 3D printing, which solves the problem that the complex structure cannot be prepared by traditional machining; and has high bonding strength between trabeculae and the matrix, therefore it is not easy to fall off, thereby improving the service life of the prosthesis. The integral ankle prosthesis containing zirconium-niobium alloy on oxidation layer of the present disclosure realizes the excellent biocompatibility of bone integration interface, bone ingrowth ability, super wear resistance and low wear rate of friction interface. There is an oxygen-rich layer between the oxidation layers of the talus part and the tibial part and the matrix, which acts as a transition layer to improve adhesion between the oxidation layer and the matrix, prevent the oxidation layer from falling off, and the oxidation layer has high hardness. The ankle prosthesis according to the present disclosure has low artifact, little interference to nuclear magnetic field and can be used for nuclear magnetic detection. No extra pad is required in the present disclosure to solve the problem of fretting between the tibial part and the liner in the existing technology.

DETAILED DESCRIPTION OF THE EMBODIMENTS

Figure 1:
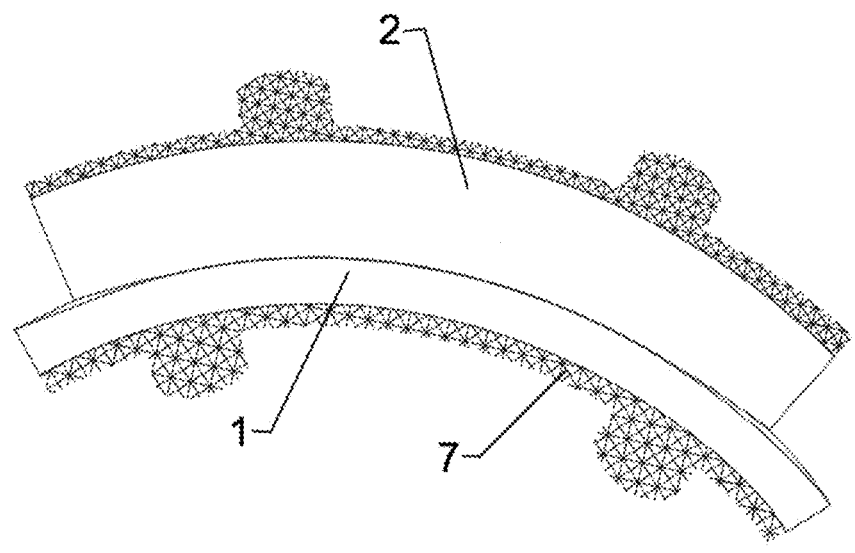
FIG. 1 is a schematic diagram of ankle prosthesis containing zirconium-niobium alloy on oxidation layer of the present disclosure.
Figure 2:
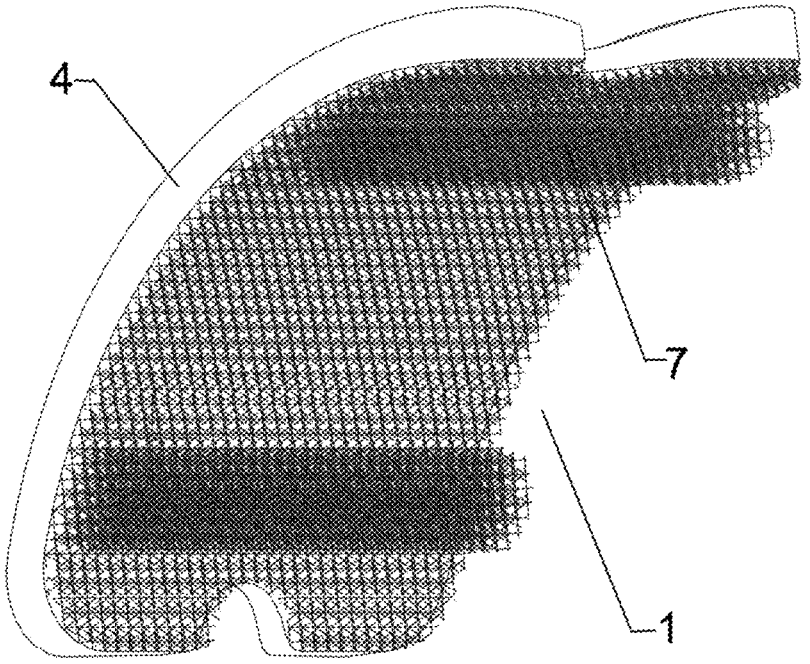
FIG. 2 is an axonometric diagram of talus part.
Figure 3:
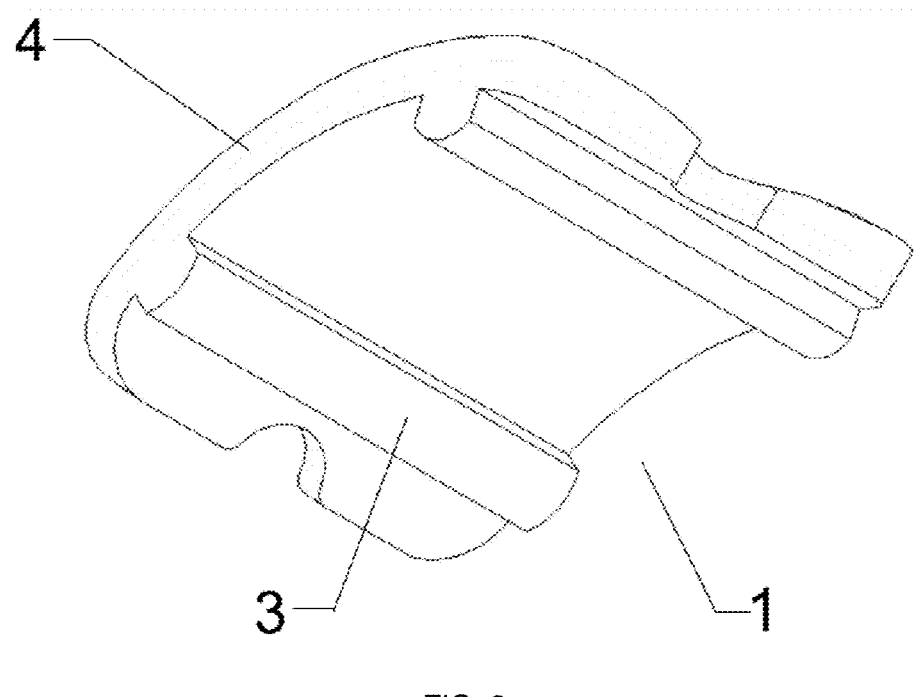
FIG. 3 is an axonometric diagram of talus part (without trabeculae).
Figure 4:
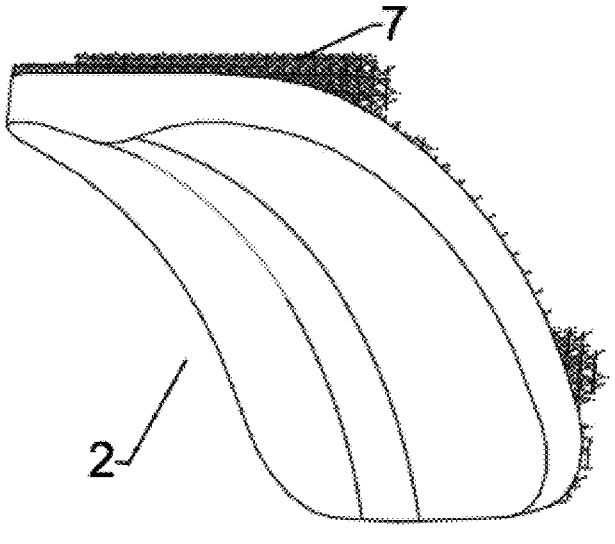
FIG. 4 is an axonometric diagram of tibial part.
Figure 5:
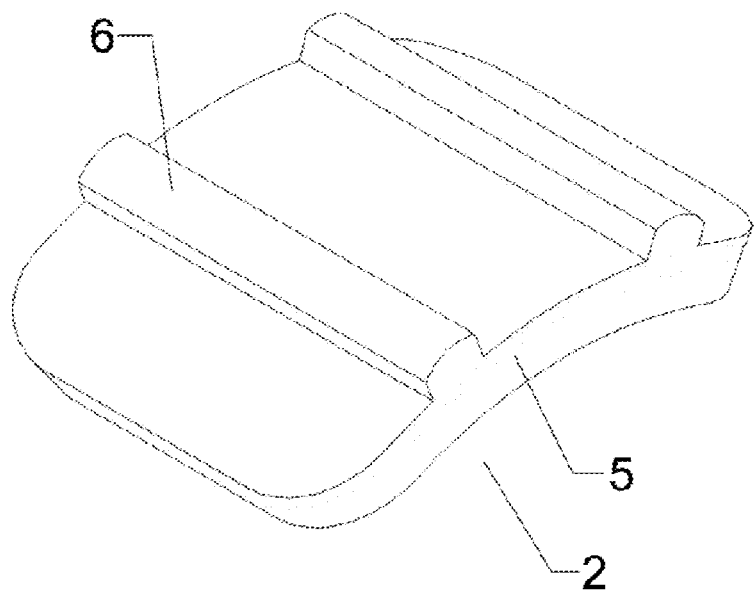
FIG. 5 is an axonometric diagram of tibial part (without trabeculae).

The present disclosure will be further described below with the drawings and embodiments.

Embodiment 1

The preparation method of the ankle prosthesis containing zirconium-niobium alloy on oxidation layer includes the following steps:

The preparation method of ankle prosthesis containing zirconium-niobium alloy on oxidation layer includes the following steps:

1) Using zirconium-niobium alloy powder as the raw material, conducting a 3D printing for one-piece molding, and obtaining a first intermediate of talus part and a first intermediate of tibial part respectively, putting the two first intermediates into the Sinter-HIP furnace, heating to 1250° C. under argon gas protection, placing at a constant pressure of 180 MPa for 3 h, reducing to a normal pressure, cooling to below 200° C. with the furnace, taking them out, and obtaining a second intermediate of talus part and a second intermediate of tibial part;

2) Placing two second intermediate products in a programmable thermostat to cool to −80° C. at a rate of 1° C./min, keeping them at a constant temperature for 10 h, and taking them out of the programmed thermostat; placing them in a liquid nitrogen for 16 h, and adjusting the temperature to a room temperature so as to obtain a third intermediate of talus part and a third intermediate of tibial part;

3) Placing two third intermediate products in a programmable thermostat to cool to −80° C. at a rate of 1° C./min, and placing them at a constant temperature for 10 h, taking them out of the programmed thermostat, placing them in the liquid nitrogen for 16 h and adjusting the temperature to room temperature so as to obtain a fourth intermediate of talus part and a fourth intermediate of tibial part;

4) Machining, finishing, polishing, cleaning, and drying the fourth intermediate products, and obtaining a fifth intermediate of talus part and a fifth intermediate of tibial part; the roughness of the upper surface of the fifth intermediate product of the talus part and the lower surface of the fifth intermediate product of the tibial part is Ra=0.012 μm;

5) Placing the two fifth intermediate products in a tube furnace, introducing normal-pressure argon gas containing 5% of oxygen in percentage by mass, heating to 500° C. at 5° C./min, and cooling down to 400° C. at 0.4° C./min; and cooling to be below 200° C. sequentially, taking them out to obtain the talus part and tibial part.

The structure of the talus part is the same as its first intermediate, second intermediate, third intermediate, fourth intermediate and fifth intermediate.

The structure of the tibial part is the same as its first intermediate, second intermediate, third intermediate, fourth intermediate, and fifth intermediate.

As shown in FIGS. 1-5, the ankle prosthesis containing zirconium-niobium alloy on oxidation layer comprises a talus part 1 and a tibial part 2, the talus part 1 comprises a talus body 4 and two first fixations 3 arranged at the front and rear direction of the lower surface of the talus body 4. The tibial part 2 comprises a tibial body 5 and two second fixations 6 arranged at the front and rear direction of the upper surface of the tibial body 5. The talus part 1 is connected with the tibial part 2 in a sliding mode.

A bone trabeculae 7 is arranged on the lower surface of the talus body 4 and the outer surfaces of the two first fixations 3, and the bone trabeculae 7 is arranged on the upper surface of the tibial body 5 and the outer surfaces of the two second fixations 6 as well, the pore size of the bone trabeculae 7 is 0.80 mm, the porosity is 72%, through-hole ratio is 100%, and the thickness is 0.5 mm.

The chemical composition of the zirconium-niobium alloy powder in percentage by mass is respectively 85.6% of Zr, 12.5% of Nb, and the rest are unavoidable impurities; where a particle size of the zirconium-niobium alloy powder ranges from 45 to 150 μm.

The specific steps for adjusting the temperature in steps 2) and 3) are: increasing the temperature to −120° C. and keeping the constant temperature for 5 h; then increasing the temperature to −40° C. and keeping the constant temperature for 5 h and then increasing the temperature to 4° C. and keeping the constant temperature for 3 h and then increasing the temperature.

The talus part 1 is installed on the root bone, and the tibial part 2 is installed on the bottom of the tibia.

Embodiment 2

The preparation method of the ankle prosthesis containing zirconium-niobium alloy on oxidation layer includes the following steps:

The preparation method of ankle prosthesis containing zirconium-niobium alloy on oxidation layer includes the following steps:

1) Using zirconium-niobium alloy powder as the raw material, conducting a 3D printing for one-piece molding, and obtaining a first intermediate of talus part and a first intermediate of tibial part respectively, putting the two first intermediates into the Sinter-HIP furnace, heating to 1325° C. under helium gas protection, placing at a constant pressure of 160 MPa for 2 h, reducing to a normal pressure, cooling to below 200° C. with the furnace, taking them out, and obtaining a second intermediate of talus part and a second intermediate of tibial part;

2) Placing two second intermediate products in a programmable thermostat to cool to −100° C. at a rate of 1° C./min, keeping them at a constant temperature for 7 h, and taking them out of the programmed thermostat; placing them in a liquid nitrogen for 24 h, and adjusting the temperature to a room temperature so as to obtain a third intermediate of talus part and a third intermediate of tibial part;

3) Placing two third intermediate products in a programmable thermostat to cool to −100° C. at a rate of 1° C./min, and placing them at a constant temperature for 7 h, taking them out of the programmed thermostat, placing them in the liquid nitrogen for 24 h and adjusting the temperature to room temperature so as to obtain a fourth intermediate of talus part and a fourth intermediate of tibial part;

4) Machining, finishing, polishing, cleaning, and drying the fourth intermediate products, and obtaining a fifth intermediate of talus part and a fifth intermediate of tibial part; the roughness of the upper surface of the fifth intermediate product of the talus part and the lower surface of the fifth intermediate product of the tibial part is Ra=0.035 μm;

5) Placing the two fifth intermediate products in a tube furnace, introducing normal-pressure helium gas containing 10% of oxygen in percentage by mass, heating to 600° C. at 15° C./min, and cooling down to 450° C. at 0.7° C./min; and cooling to be below 200° C. sequentially, taking them out to obtain the talus part and tibial part.

The structure of the talus part is the same as its first intermediate, second intermediate, third intermediate, fourth intermediate and fifth intermediate.

The structure of the tibial part is the same as its first intermediate, second intermediate, third intermediate, fourth intermediate, and fifth intermediate.

The ankle prosthesis containing zirconium-niobium alloy on oxidation layer comprises a talus part 1 and a tibial part 2, the talus part 1 comprises a talus body 4 and two first fixations 3 arranged at the front and rear direction of the lower surface of the talus body 4. The tibial part 2 comprises a tibial body 5 and two second fixations 6 arranged at the front and rear direction of the upper surface of the tibial body 5. The talus part 1 is connected with the tibial part 2 in a sliding mode. A bone trabeculae 7 is arranged on the lower surface of the talus body 4 and the outer surfaces of the two first fixations 3, and the bone trabeculae 7 is arranged on the upper surface of the tibial body and the outer surfaces of the two second fixations 6 as well, the pore size of the bone trabeculae 7 is 0.35 mm, the porosity is 55%, through-hole ratio is 100%, and the thickness is 1.5 mm.

The chemical composition of the zirconium-niobium alloy powder in percentage by mass is respectively 93.4% of Zr, 5.1% of Nb, and the rest are unavoidable impurities; where a particle size of the zirconium-niobium alloy powder ranges from 45 to 150 µm.

The specific steps for adjusting the temperature in steps 2) and 3) are: increasing the temperature to −100° C. and keeping the constant temperature for 4 h; then increasing the temperature to −30° C. and keeping the constant temperature for 4 h and then increasing the temperature to 6° C. and keeping the constant temperature for 2 h and then increasing the temperature.

Embodiment 3

The preparation method of the ankle prosthesis containing zirconium-niobium alloy on oxidation layer includes the following steps:

The preparation method of ankle prosthesis containing zirconium-niobium alloy on oxidation layer includes the following steps:

1) Using zirconium-niobium alloy powder as the raw material, conducting a 3D printing for one-piece molding, and obtaining a first intermediate of talus part and a first intermediate of tibial part respectively, putting the two first intermediates into the Sinter-HIP furnace, heating to 1400° C. under argon gas protection, placing at a constant pressure of 140 MPa for 1 h, reducing to a normal pressure, cooling to below 200° C. with the furnace, taking them out, and obtaining a second intermediate of talus part and a second intermediate of tibial part;

2) Placing two second intermediate products in a programmable thermostat to cool to −120° C. at a rate of 1° C./min, keeping them at a constant temperature for 5 h, and taking them out of the programmed thermostat; placing them in a liquid nitrogen for 36 h, and adjusting the temperature to a room temperature so as to obtain a third intermediate of talus part and a third intermediate of tibial part;

3) Placing two third intermediate products in a programmable thermostat to cool to −120° C. at a rate of 1° C./min, and placing them at a constant temperature for 5 h, taking them out of the programmed thermostat, placing them in the liquid nitrogen for 36 h and adjusting the temperature to room temperature so as to obtain a fourth intermediate of talus part and a fourth intermediate of tibial part;

4) Machining, finishing, polishing, cleaning, and drying the fourth intermediate products, and obtaining a fifth intermediate of talus part and a fifth intermediate of tibial part; the roughness of the upper surface of the fifth intermediate product of the talus part and the lower surface of the fifth intermediate product of the tibial part is Ra=0.050 µm;

5) Placing the two fifth intermediate products in a tube furnace, introducing normal-pressure argon gas containing 15% of oxygen in percentage by mass, heating to 700° C. at 20° C./min, and cooling down to 495° C. at 0.9° C./min; and cooling to be below 200° C. sequentially, taking them out to obtain the talus part and tibial part.

The structure of the talus part is the same as its first intermediate, second intermediate, third intermediate, fourth intermediate and fifth intermediate.

The structure of the tibial part is the same as its first intermediate, second intermediate, third intermediate, fourth intermediate, and fifth intermediate.

The ankle prosthesis containing zirconium-niobium alloy on oxidation layer comprises a talus part 1 and a tibial part 2, the talus part 1 comprises a talus body 4 and two first fixations 3 arranged at the front and rear direction of the lower surface of the talus body 4. The tibial part 2 comprises a tibial body 5 and two second fixations 6 arranged at the front and rear direction of the upper surface of the tibial body 5. The talus part 1 is connected with the tibial part 2 in a sliding mode. A bone trabeculae 7 is arranged on the lower surface of the talus body 4 and the outer surfaces of the two first fixations 3, and the bone trabeculae 7 is arranged on the upper surface of the tibial body and the outer surfaces of the two second fixations 6 as well, the pore size of the bone trabeculae 7 is 1.10 mm, the porosity is 78%, through-hole ratio is 100%, and the thickness is 3 mm.

The chemical composition of the zirconium-niobium alloy powder in percentage by mass is respectively 96.5% of Zr, 1.0% of Nb, and the rest are unavoidable impurities; where a particle size of the zirconium-niobium alloy powder ranges from 45 to 150 µm.

The specific steps for adjusting the temperature in steps 2) and 3) are: increasing the temperature to −80° C. and keeping the constant temperature for 3 h; then increasing the temperature to −20° C. and keeping the constant temperature for 3 h and then increasing the temperature to 8° C. and keeping the constant temperature for 1 h and then increasing the temperature.

Control Group 1

Using zirconium-niobium alloy powder as Embodiment 1 as a raw material, conducting a 3D printing for one-piece molding, and obtaining ankle prosthesis which structure is same as that of the Embodiment 1.

Experiment Verification

Figure 6:
FIG. 6 shows the metallographic micro structure of the solid part of the tibial part in Control Group 1, wherein A is observed by 50 times magnification; B is observed by 500 times magnification.
Figure 6:
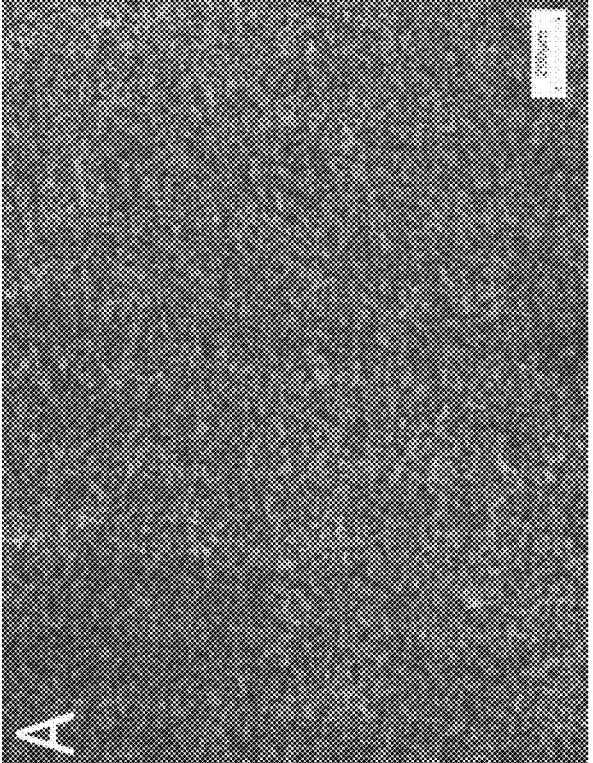
Figure 7:
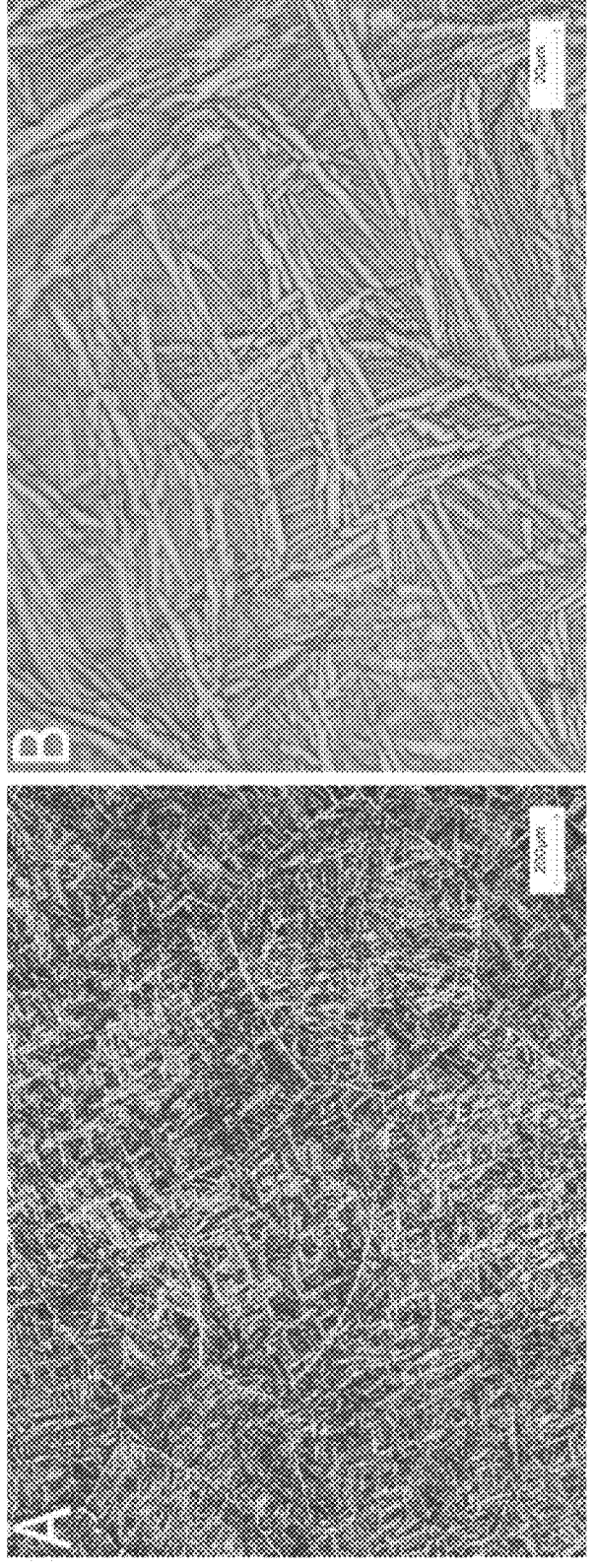
FIG. 7 shows the metallographic microscopic structure of the solid body of the tibial part in Embodiment 1 that has not been prepared with step 4) and step 5) in the preparation method.

A solid part of the tibial part in the control group 1 and a tibial part of the embodiment 1 that has not been prepared with step 4) and 5) were observed and analyzed by an inverted scanning electron microscope (Axio Vert.A1, Zeiss, Germany). The results were shown in FIGS. 6-7. In the metallographic photos of the tibial part of the Control Group 1, small a martensite can be observed. The structure is small, easy for stress concentration, and the plasticity is poor. In the metallograph of tibial part of the Embodiment 1, a phase can be observed, basket net structure, grain refinement. The results indicated that the solid part (without oxidation layer) of the tibial part of the ankle prosthesis of the present disclosure has excellent strength and plasticity.

Figure 8:
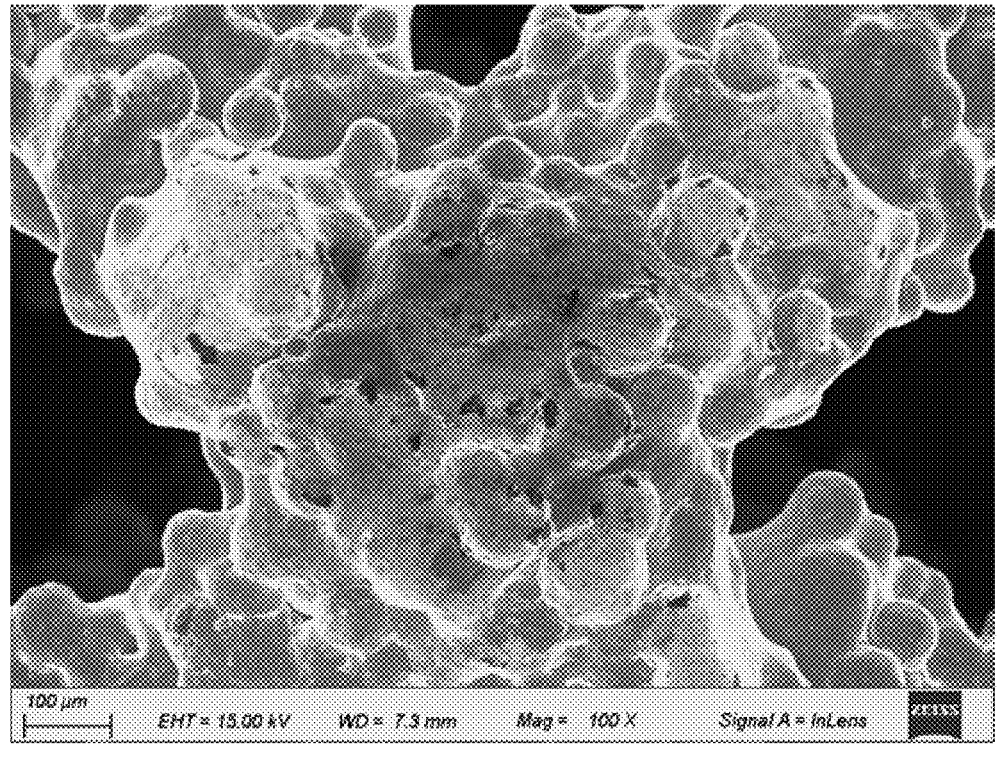
FIG. 8 shows the SEM of bone trabeculae of the tibial part of Control Group 1.
Figure 9:
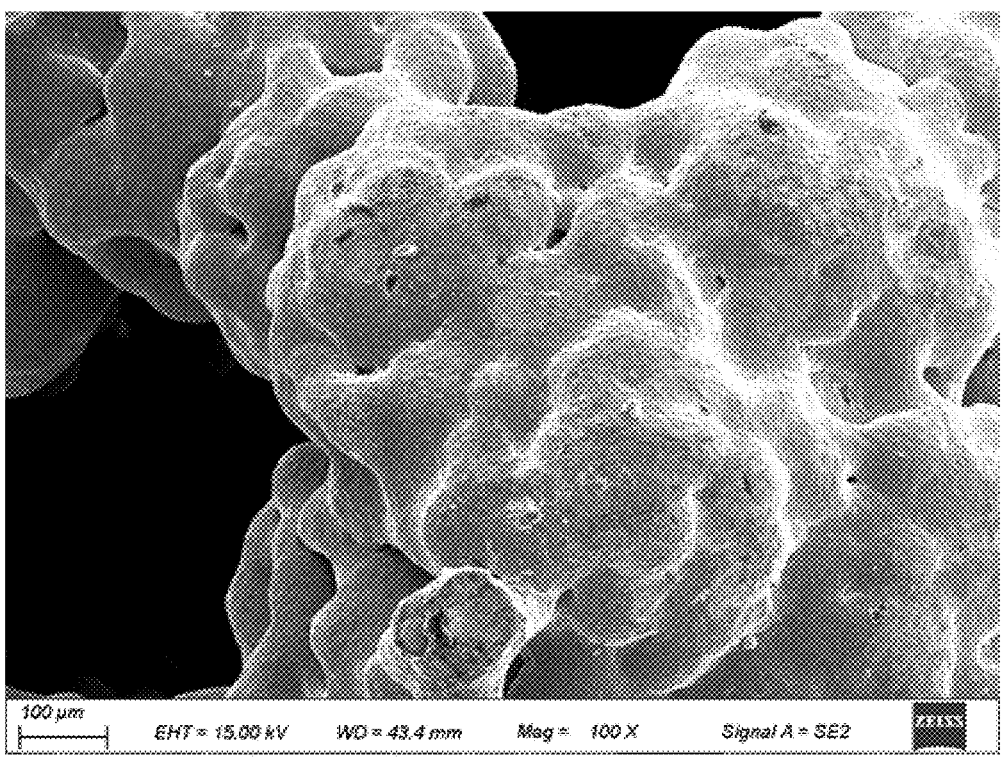
FIG. 9 shows the SEM of bone trabeculae of the tibial part in Embodiment 1 that has not been prepared with step 4) and step 5) in the preparation method.

The bone trabeculae of the tibial part in the control group 1 and the bone trabeculae of the tibial part of the embodiment 1 that has not been prepared with step 4) and 5) were observed and analyzed by scanning electron microscopy (Crossbeam 340/550, Zeiss, Germany), the results are shown in FIGS. 8-9. Compared with the Control Group 1, the zirconium-niobium alloy powder in the bone trabecula structure of Embodiment 1 was further sintered, indicating that a combination property of the bone trabeculae was improved.

A physical compression test piece (size: 8*8*10 mm³) of tibial part the that has not been prepared with step 1-4) and 1-5) in the preparation method in the embodiment 1 and a physical compression test piece (size: 8*8*10 mm³) of the tibial part in the control group 1 were subjected to a compression performance test by an electronic universal testing machine (UTM5105, Shenzhen SUNS Technology Co., Ltd., and China). There were 5 physical compression test pieces respectively in the embodiment 1 and the control group 1. Results were shown in Table 1. The compressive yield strength of embodiment 1 is 546.72 MPa, better than that of Control Group 1 (P<0.05), suggesting that the solid part of the tibial part prepared by the present disclosure has excellent anti-compression performance.

TABLE 1

| | | | |
|---|---|---|---|
| Anti-compression experiment results of the solid specimens of Control Group 1 and Embodiment 1 ($\bar{x}$ + s, n = 5, *P < 0.05, compared with Control Group 1) | | | |
| Group | Cross-sectional Area (mm$^2$) | Yield Load (kN) | Yield Strength (MPa) |
| Embodiment 1 | 64 | 34.99 ± 4.04* | 546.72 ± 63.19* |
| Control Group 1 | 64 | 23.59 ± 2.30 | 368.63 ± 35.92 |

A bone trabecula compression specimens with pore size of 0.80 mm, porosity of 72% and through-hole rate of 100% of the tibial part of the Control Group 1 and the bone trabecula compression specimens with pore size of 0.80 mm, porosity of 72% and through-hole rate of 100% of the tibial part of Embodiment 1 (specimen size: 8*8*10 mm$^3$) that has not been prepared with step 4) and step 5) of the above-mentioned preparation method, were subjected to a compression test by the electronic universal testing machine (UTM5105, Shenzhen SUNS Technology Co., Ltd., and China). Bone trabecula compression specimens of the Control Group 1 and the Embodiment 1 were 5 pieces each. The results are shown in Table 2. The compressive yield strength of Embodiment 1 is 18.39 MPa, significantly better than that of Control Group 1 (P<0.05), suggesting that the bone trabecular part of the tibial part prepared by the present disclosure has excellent anti-compression performance.

TABLE 2

| | | | |
|---|---|---|---|
| Anti-compression experiment results of the bone trabecular specimens of Control Group 1 and Embodiment 1 ($\bar{x}$ + s, n = 5, *P < 0.05, compared with Control Group 1) | | | |
| Group | Cross-sectional Area (mm$^2$) | Yield Load (N) | Yield Strength (MPa) |
| Embodiment 1 | 64 | 1177.24 ± 91.66* | 18.39 ± 1.43* |
| Control Group 1 | 64 | 926.12 ± 106.13 | 14.47 ± 1.66 |

Figure 10:
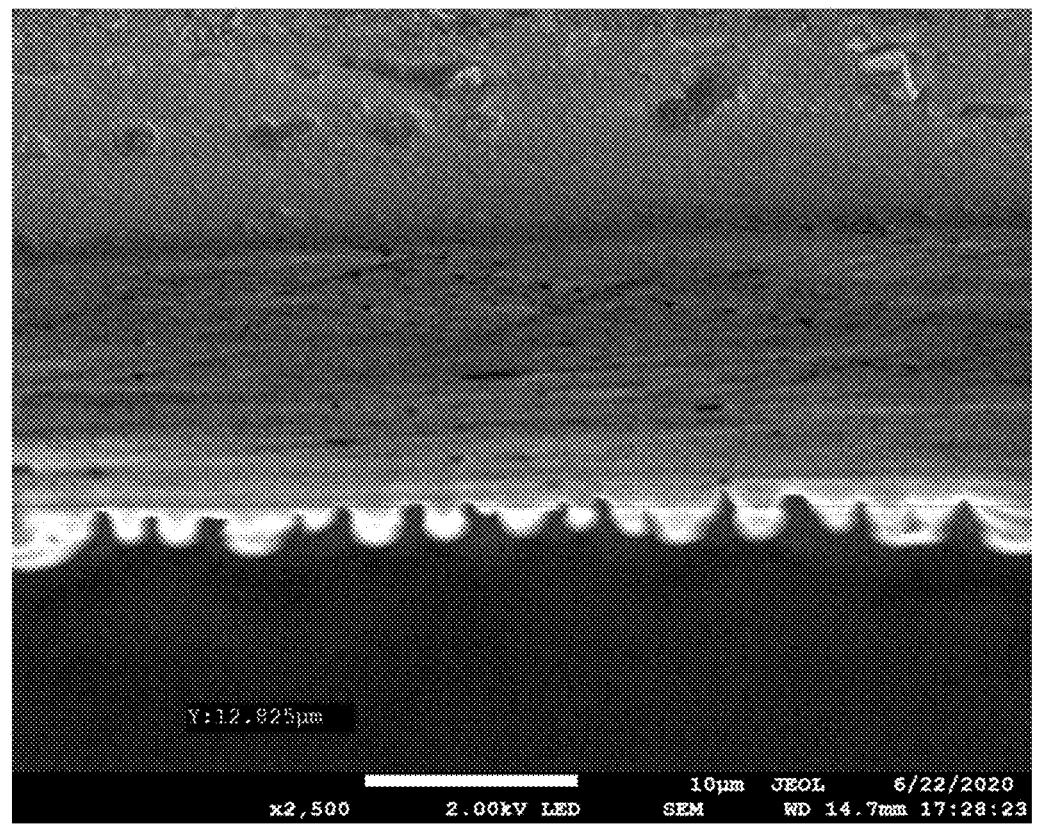
FIG. 10 shows the SEM of cross section of oxidation layer of the tibial part and matrix in Embodiment 1.

The cross-section of the matrix and oxidation layer of the zirconium-niobium alloy of the tibial part of the Embodiment 1 was observed by scanning electron microscopy (Crossbeam 340/550, Zeiss, Germany) (see FIG. 10). The cross sections of the matrix and oxidation layer of the zirconium-niobium alloy in Embodiments 2 and 3 were observed. The oxidation layer thickness were 10.3 μm, 17.2 μm and 20.6 μm, respectively.

There was an oxygen-rich layer between the oxidation layer and the matrix of the zirconium-niobium alloy to enhance the bonding force between the matrix and oxidation layer of zirconium-niobium alloy.

Figure 11:
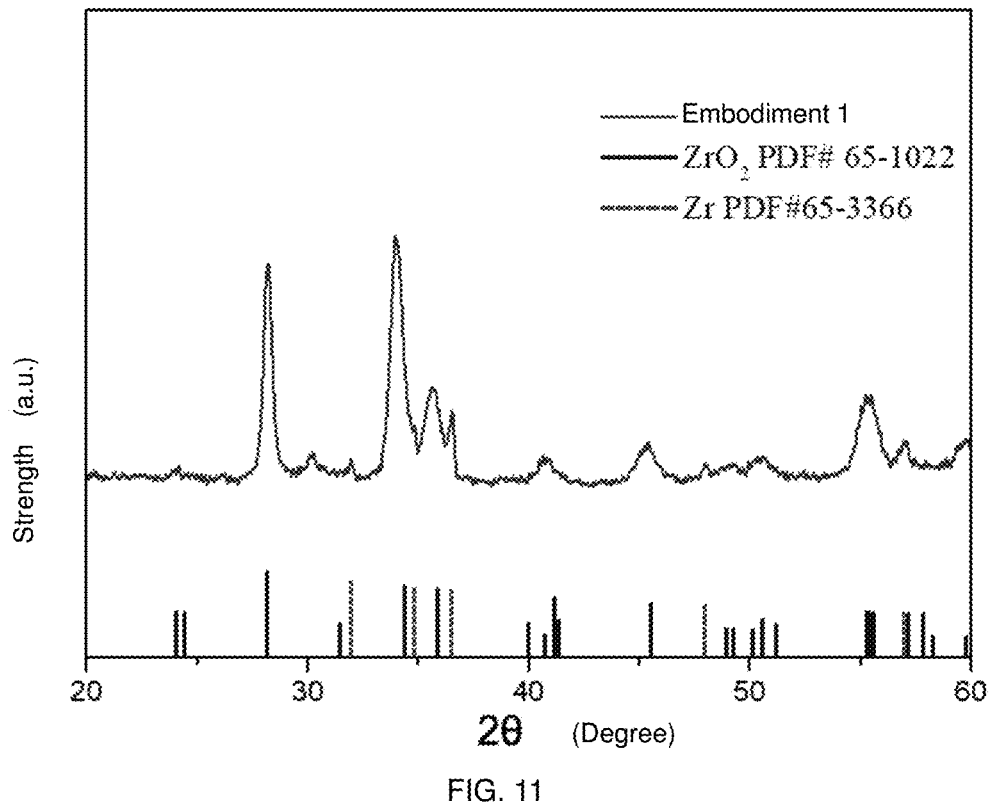
FIG. 11 shows the XRD curve of oxidation layer surface of the tibial part in Embodiment 1.

XRD (D8DISCOVER, Bruker, Germany) analyzed the oxidation layer of the tibial part of Embodiment 1 (FIG. 11). The oxidation layer contained monoclinic phase zirconia and tetragonal phase zirconia.

The microhardness measurement on the tibial part of Embodiments 1-3 was determined by a microhardness tester (MHVS-1000 PLUS, Shanghai Aolongxingdi Testing Equipment Co., Ltd., China), in which the load was 0.05 kg, the load time of the specimens was 20 s, and 8 points were taken for each specimen. The average hardness values measured in Embodiments 1-3 were 1948.6 Hv, 1923.7 Hv, and 1967.2 Hv, suggesting that the oxidation layer of the tibial part in the ankle prosthesis of the present disclosure has high hardness.

Experiments have proved that the zirconium-niobium alloy powder bonding degree, compressive properties, compressive properties and metallographic structure of the solid part, the crystal structure of the oxidation layer, thickness and hardness of the oxidation layer for the tibial part and the talus part prepared in Embodiments 2 and 3 are similar to that of the tibial part prepared in Embodiment 1.

The invention claimed is:

1. A preparation method of an ankle prosthesis containing zirconium-niobium alloy on an oxidation layer comprising the following steps:

1) using zirconium-niobium alloy powder as the raw material, conducting a 3D printing for one-piece molding, and obtaining a first intermediate of talus part and a first intermediate of tibial part respectively, putting the two first intermediates into the Sinter-HIP furnace, heating to 1250° C.-1400° C. under helium/argon gas protection, placing at a constant pressure of 140 MPa-180 MPa for 1 h to 3 h, reducing to a normal pressure, cooling to below 200° C. with the furnace, taking them out, and obtaining a second intermediate of talus part and a second intermediate of tibial part;

2) placing the second intermediate of the talus part and the second intermediate of the tibial part in a programmable thermostat to cool to −80° C. to −120° C. at a rate of 1° C./min, keeping them at a constant temperature for 5 h to 10 h, and taking them out of the programmed thermostat; placing them in a liquid nitrogen for 16 h to 36 h, and adjusting the temperature to a room temperature so as to obtain a third intermediate of talus part and a third intermediate of tibial part;

3) placing the third intermediate of the talus part and the third intermediate of the tibial part in a programmable thermostat to cool to −80° C. to −120° C. at a rate of 1° C./min, and placing them at a constant temperature for 5 h to 10 h, taking them out of the programmed thermostat, placing them in the liquid nitrogen for 16 h to 36 h and adjusting the temperature to room temperature so as to obtain a fourth intermediate of talus part and a fourth intermediate of tibial part;

4) machining, finishing, polishing, cleaning, and drying the fourth intermediate products fourth intermediate of the talus part and the fourth intermediate of the tibial part, and obtaining a fifth intermediate of talus part and a fifth intermediate of tibial part; the roughness of the upper surface of the fifth intermediate product of the talus part and the lower surface of the fifth intermediate product of the tibial part is Ra≤0.050 μm;

5) placing the fifth intermediate of the talus part and the fifth intermediate of the tibial part in a tube furnace, introducing normal-pressure helium/argon gas containing 5% to 15% of oxygen in percentage by mass, heating to 500° C. to 700° C. at 5° C./min to 20° C./min, and cooling down to 400° C. to 495° C. at 0.4° C./min to 0.9° C./min; and cooling to be below 200° C. sequentially, taking them out to obtain the talus part and tibial part;

the structure of the talus part is the same as its first intermediate, second intermediate, third intermediate, fourth intermediate and fifth intermediate;

the structure of the tibial part is the same as its first intermediate, second intermediate, third intermediate, fourth intermediate, and fifth intermediate;

the ankle prosthesis containing zirconium-niobium alloy on the oxidation layer comprises a talus part (1) and a tibial part (2), the talus part (1) comprises a talus body (4) and two first fixations (3) arranged at the front and rear direction of the lower surface of the talus body (4);

the tibial part (2) comprises a tibial body (5) and two second fixations (6) arranged at the front and rear direction of the upper surface of the tibial body (5);

the talus part (1) is connected with the tibial part (2) in a sliding mode;

a bone trabeculae (7) is arranged on the lower surface of the talus body (4) and the outer surfaces of the two first fixations (3), and the bone trabeculae (7) is arranged on the upper surface of the tibial body (5) and the outer surfaces of the two second fixations (6) as well, the pore size of the bone trabeculae (7) ranges from 0.35 mm-1.10 mm, the porosity ranges from 55% to 78%, through-hole ratio is 100%, and the thickness ranges from 0.5 mm-3 mm.

2. The preparation method according to claim 1, wherein the chemical composition of the zirconium-niobium alloy powder in percentage by mass is respectively 85.6%-96.5% of Zr, 1.0%-12.5% of Nb, and the rest are unavoidable impurities; where a particle size of the zirconium-niobium alloy powder ranges from 45 to 150 µm.

3. The preparation method according to claim 1, wherein the specific steps for adjusting the temperature in steps 2) and 3) are: increasing the temperature to −120° C. to −80° C. and keeping the constant temperature for 3 h to 5 h; then increasing the temperature to −40° C. to −20° C. and keeping the constant temperature for 3 h to 5 hand then increasing the temperature to 4° C. to 8° C. and keeping the constant temperature for 1 h to 3 h and then increasing the temperature.

4. The ankle prosthesis containing zirconium-niobium alloy on the oxidation layer prepared by the preparation method according to claim 1.

5. The ankle prosthesis containing zirconium-niobium alloy on the oxidation layer prepared by the preparation method according to claim 2.

6. The ankle prosthesis containing zirconium-niobium alloy on the oxidation layer prepared by the preparation method according to claim 3.

* * * * *